United States Patent
Fujita (10) Patent No.: US 6,535,621 B1
(45) Date of Patent: Mar. 18, 2003

(54) DEFECT INTEGRATED PROCESSING APPARATUS AND METHOD THEREOF

(75) Inventor: Minoru Fujita, Kawasaki (JP)

(73) Assignee: Toshiba Engineering Corporation, Kawasaki (JP)

( * ) Notice: Subject to any disclaimer, the term of this patent is extended or adjusted under 35 U.S.C. 154(b) by 0 days.

(21) Appl. No.: 09/285,748

(22) Filed: Apr. 5, 1999

(30) Foreign Application Priority Data

Jul. 21, 1998 (JP) ............................................. 10-205253

(51) Int. Cl.[7] ................................................ G06K 9/00
(52) U.S. Cl. ...................... 382/112; 382/141; 382/149; 250/559.4
(58) Field of Search ................................. 382/112, 100, 382/149, 141; 250/559.4; 356/238.1; 700/130; 348/127

(56) References Cited

U.S. PATENT DOCUMENTS

| 5,068,799 | A | * | 11/1991 | Jarrett ........................ 364/507 |
| 5,091,963 | A | * | 2/1992 | Litt et al. ....................... 382/8 |
| 5,774,177 | A | * | 6/1998 | Lane ............................ 348/88 |
| 6,091,847 | A | * | 7/2000 | Chiu et al. .................... 342/149 |
| 6,236,057 | B1 | * | 5/2001 | Shishido et al. ............ 250/559 |

FOREIGN PATENT DOCUMENTS

| EP | 0 311 991 A2 | 4/1989 |
| EP | 0 428 751 A1 | 5/1991 |

OTHER PUBLICATIONS

European Search Report dated Jan. 28, 2000.

* cited by examiner

*Primary Examiner*—Bhavesh Mehta
*Assistant Examiner*—Barry Choobin
(74) *Attorney, Agent, or Firm*—McGinn & Gibb, PLLC (57) ABSTRACT

A defect integrated processing apparatus and method for performing a processing in an integrated fashion of various kinds of edfect and then detecting the accurate number, positions, sizes, etc. of the defects in detail, includes detecting light-and-shade defects based on an image data obtained by picking up an object to be inspected. Edges and minute defect on the object are detected by performing a differential processing of the image data, low contrast light-and-shade defects are detected by performing an integral processing of the image data obtained through the image pick-up device and then a differential processing of an obtained integrated image, and an integrated information of defects is obtained by performing a processing in an integrated fashion of detected defects.

21 Claims, 7 Drawing Sheets

PROJECTION DATA

SMOOTHED DATA

| 1 | 1 | 1 | 0 | 0 | 0 | 1 | 1 | 1 |

DEFECT INTEGRATED PROCESSING APPARATUS AND METHOD THEREOF

BACKGROUND OF THE INVENTION

1. Field of the Invention

The present invention relates to a defect integrated processing apparatus for performing an integrated processing of light and shade and/or smudgy defects and method thereof.

More particularly, the invention relates to a defect integrated processing apparatus and method for use in inspection of defects on a plain material roll (or web) based on an image data which is produced by an image pick-up camera, picking up an image of the web (e.g., paper, film and nonwoven fabric, etc.) having a certain width and traveling in one direction,

2. Description of the Related Art

Conventionally, various inspection apparatuses are well known. In a typical inspection apparatus, an image of a workpiece such as a web is picked up by using a camera and light-and-shade or minute defects of the workpiece are inspected through the use of an image signal obtained by the camera.

Figure 16:
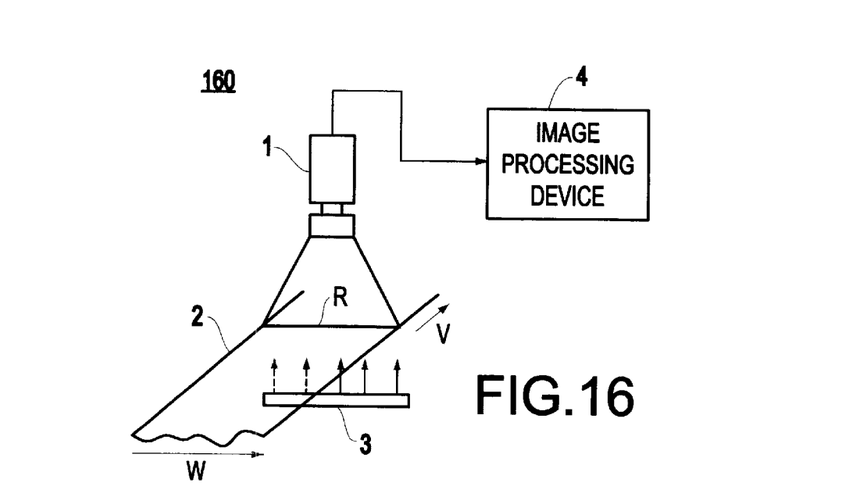
FIG. 16 is a schematic diagram showing a conventional defect inspection apparatus 160.

For example, FIG. 16 is a block diagram showing a conventional light-and-shade inspection apparatus 160. Apparatus 160 includes a line-sensor camera 1 for picking up an image of a web 2 as an inspected object having a constant width and traveling in one direction, an illuminator 3 for illuminating a zone R picked up by the camera 1, and an image processing device 4 for processing data of an image picked up by the camera 1 and inspecting a defect on the web.

The line-sensor camera 1 includes, for example, a photodetector array of 1024 elements (e.g., a charge-coupled device (CCD)) disposed along a line. Specifically, the camera 1 is disposed upwardly of a central portion along a width (or transverse) direction of the web so that the photodetectors are arranged in a line array across the web in the transverse (width) direction thereof and in parallel with the transverse direction. The illuminator 3 is disposed downwardly of (e.g., beneath) the web 2 so as to illuminate the zone R to be picked up by the camera 1 from a rear surface of the web 2.

The image processing device 4 detects a light-and-shade defect by judging whether an obtained image data such as a brightness (e.g., luminance) information is more than a predetermined value, or detects low contrast light-and-shade defects such as crevice spots and oil stains, etc., by, as a macro-filter processing, segmenting (e.g., partitioning) an image data at every predetermined range to form a plurality of segments and performing an integration within the respective segments. Thereafter, a differentiation is performed by obtaining respective differences between segments of those integration values, or, functions to detect edges and minute defects by a micro-filter processing, using a differentiating filter processing.

However, such a conventional inspection apparatus 160 is limited to a processing operation for separately or independently detecting those various defects. Thus, in the conventional inspection apparatus, a defect may be detected to be defects of more than one kind on the workpiece (e.g., a defect may be counted as a first type of defect and as a second type of defect, even though the defect constitutes a single defect). As a result, the number of defects may be incorrectly detected (e.g., to be greater than an actual number of defects).

Additionally, it is impossible to know from the detected results which features, such as an actual profile and size, etc., the respective defects as detected have on the workpiece. Further, in the detection of the low contrast light-and-shade defect by using the macro-filter processing, the presence and the absence of defects are detected at each segment (e.g., at a segment unit) defining an integrating range. Consequently, a spatial resolution becomes coarse depending on how segments on the image data are established. Thus, accurately detecting defect positions and sizes is difficult.

SUMMARY OF THE INVENTION

In view of the foregoing and other problems of the conventional systems and methods, an object of the present invention is to provide a defect integrated processing apparatus and method thereof capable of precisely detecting and obtaining a defect information including, for example, number, position and/or size of the defects, etc., by integrally processing various kinds of defects.

To overcome the above-mentioned problem and others, in a first aspect, a defect integrated processing apparatus according to the present invention for use in picking up an image of an object to be inspected to obtain an image data and then, based on the image data, inspecting defects on the object in an integrated fashion, includes:

an image pick-up device for picking up an image of an object to output an image data;

a light-and-shade defect detecting portion for detecting light-and-shade defects on the object based on the image data obtained through the image pick-up device;

a minute defect detecting portion for detecting edges and minute defects on the object by performing a differential processing of the image data obtained through the image pick-up device;

a low contrast light-and-shade defect detecting portion for performing a differential processing of an integrated image obtained through an integral processing of the image data obtained through the image pick-up device; and a defect integrated processing portion for obtaining an integrated information involving defects by performing a processing, in an integrated fashion, of the respective defects of the light-and-shade defects obtained through the light-and-shade defect detecting portion, the minute defects obtained from the minute defect detecting portion, and the low contrast light-and-shade defects obtained through the low contrast light-and-shade defect detecting portion.

With this arrangement, various kinds of defects are processed in an integrated fashion to allow a detailed detection to obtain an accurate defect information about, for example, a number of defects, positions of defects, and/or sizes thereof, etc.

Also, according to the present invention, the light-and-defect detecting portion includes:

a projection operation portion for calculating a projection data by adding together a predetermined number of image data at a given position along a certain direction of the object, which image data are obtained through the image pick-up device;

a background operation portion for calculating a background lightness across a width direction of the object, based on the projection data obtained through the projection operation portion; and a difference operation portion for removing variations of the background lightness across the width direction obtained through the background lightness operation portion from the image data obtained through the image pick-up device by subtracting a former background lightness from a latter image data.

With this arrangement, variations of the background lightness caused by the camera's and illuminator's optical systems and the sizes of defects, can be eliminated precisely, thereby achieving a highly reliable defect integrated processing.

Also, according to the present invention, the background lightness operation portion includes:

a filter for performing a smoothing processing of the projection data across the width direction of the object obtained through the projection operation portion; and a normalizing portion for calculating the background lightness by dividing the smoothed data through the filter by the predetermined number used for adding together the image data at the given position.

With the projection operation portion, the number of data which are processed through smoothing can be increased substantially, thereby increasing the length of the smoothed data in comparison with the defect size. Therefore, an affect of the defects on the background lightness calculation by the smoothing processing, can be reduced, thereby performing a highly accurate background lightness calculation.

Additionally, the defect integrated processing apparatus, according to the present invention, further may include a comparing portion for comparing the output of the difference operation portion with a predetermined value to detect the light-and-shade defects. With this arrangement, the light-and-shade defects can be detected reliably.

Further, in the defect integrated processing apparatus according to the present invention, the light-and-shade defect detecting portion may include a light-and-shade feature detecting portion for detecting light-and-shade features by establishing on an image based on the image data a mesh pattern of meshes, each mesh being a predetermined size, and then counting the number of pixels, each pixel being present within each mesh and larger than a light defect threshold value and similarly counting the number of pixels, each pixel being present within each mesh and smaller than a shade defective threshold value.

Further, in the defect integrated processing apparatus according to the present invention, the low contrast light-and-shade defect detecting portion may include a macro-filter processing portion, the macro-filter processing portion including:

an integrating operation portion for obtaining an integrated image by dividing an image including image data outputted from the image pick-up device into a plurality of meshes which are of substantially equivalent areas to each other and then adding together the image data present within each divided mesh;

a differentiating; operation portion for obtaining a differentiated image by performing a difference operation at every predetermined interval between meshes in connection with the integrated image obtained by the integrating operation portion; and a contrast defect detecting portion for detecting low contrast defects based on the differentiated image obtained by the differentiating operation portion.

With such a macro-filter, low contrast light-and-shade defects such as an oil stain, contaminant, mark, etc. can be detected with high accuracy.

Further, in the defect integrated processing apparatus according to the present invention, the low contrast light-and-shade defect detecting portion may include a plurality of macro-filter processing portions similar to the above-mentioned macro-filter processing portion, the macro-filter processing portions being different from each other in mesh size in a range of which the addition of the image data is performed by the integrating operation portion and different from each other in threshold value which is varied dependent on the mesh size and based on which defects are detected by the contrast defect detecting portion.

Furthermore, in the defect integrated processing apparatus according to the present invention, the low contrast defect detecting portion further may include a macro-filter integrated processing portion, the macro-filter integrated processing portion being adapted for, among meshes of different sizes in each range of which the addition of the image data is performed by the integrating operation portion, subtracting from a value of the integrated image having defects and obtained through a smaller mesh size its average value so as to obtain a subtracted value, subtracting the subtracted value from a value of the integrated image obtained through a larger mesh size so as to obtain a differentiated image in the larger mesh size, and, based on the differentiated image, judging and detecting low contrast defects in the larger mesh size.

With this arrangement, for example, a defect detected through a smaller mesh may be prevented from being again detected as another, different defect detected through a larger mesh, thereby preventing counting a defect twice. Thus, the number of defects counted will not include the same, duplicate defect.

Further, in the defect integrated processing apparatus according to the present invention, the macro-filter integrated processing portion is adapted for outputting to the defect integrated processing portion the respective values, as macro-defect features, based on the integrated images involving defects obtained through the macro-filter integrated processing portion as well as the information of mesh positions.

Further, in the defect integrated processing apparatus according to the present invention, the minute defect detecting portion may include:

a micro-filter processing portion adapted for obtaining vertical and horizontal differentiated images of an image based on the image data, calculating an added image which is an average of sum of the vertical and horizontal differentiated images, and highlighting a minute defect by smoothing the added image; and a micro-filter feature detecting portion adapted for digitizing into binary values the output value from the micro-filter processing portion, establishing a mesh pattern of meshes, each being of a predetermined size on the image based on the image data, and counting the number of pixels, each pixel having the output value which is larger than the threshold value at each mesh.

With this micro-filter, a minute defect such as a liner defect can be detected reliably.

Further, in the defect integrated processing apparatus according to the present invention, the threshold value includes plural kinds of values (e.g., three kinds of values), at each of which the number of pixels is counted.

Further, in the defect integrated processing apparatus according to the present invention, the object to be inspected may include a web having a constant width and traveling in a constant direction, and the image pick-up device may include a line-sensor camera opposed to the object and disposed across the width direction thereof.

Further, in the defect integrated processing apparatus according to the present invention, the defect integrated processing portion may include:

a connectivity analyzing portion adapted for analyzing a connectivity among the light-and-shade defects obtained by the light-and-shade defect detecting portion, the minute defects obtained through the minute defect detecting portion, and the low contrast light-and-shade defects obtained by the low contrast light-and-shade defect detecting portion; and a defect feature calculating portion adapted for calculating a predetermined feature based on one defect obtained through the connectivity analyzing portion.

With such an arrangement, for example, an area, a height and a width of a circumscribed polygon (e.g., rectangle), an aspect ratio, a compactness, a structure parameter, an edge strength, and an average density which correspond to the number of various defective pixels constituting one defect, may be obtained, thereby to obtain integrated defect information.

Furthermore, in another aspect of the present invention, a defect integrated processing method for picking up an image of an object to be inspected and then, based on its image data, inspecting in an integrated fashion defects of the object, includes:

picking up an image of an object to be inspected to obtain an image data;

based on light-and-shade information of the image data obtained through the image picking-up step, detecting light-and-shade defects of the object;

performing a differential processing of the image data obtained through the image picking-up step to detect edges and minute defects of the object;

performing an integral processing of the image data obtained through the image picking-up step to obtain an integrated image and then performing a differential processing of the obtained integrated image to detect low contrast light-and-shade defects; and performing a processing in an integrated fashion of the light-and-shade defect, the minute defects, and the low contrast light-and-shade defects detected to obtain an integrated information of defects detected.

The present disclosure relates to subject matter contained in Japanese Patent Application No. 10-205253, filed Jul. 21, 1998, which is expressly incorporated herein by reference in its entirety.

BRIEF DESCRIPTION OF THE DRAWINGS

The above and other objects, features and advantages of the present invention will become apparent from the following detailed description of the invention taken in conjunction with the accompanying drawings in which.

DETAILED DESCRIPTION OF A PREFERRED EMBODIMENT OF THE PRESENT INVENTION

Hereinafter, a preferred embodiment of the present invention will be described in detail with reference to the accompanying drawings.

Figure 1:
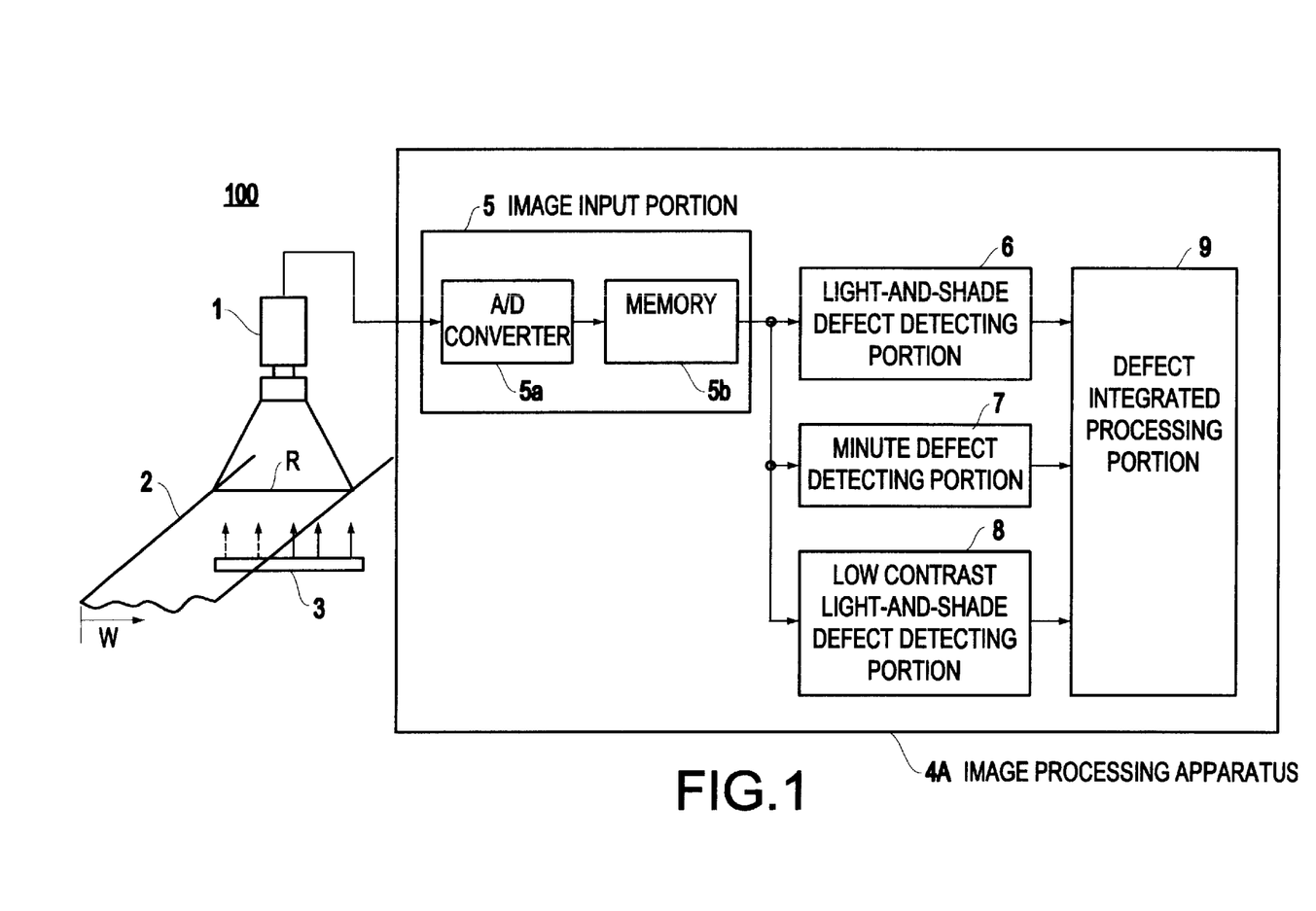
FIG. 1 is a functional block diagram showing a preferred embodiment of a defect integrated processing apparatus 100 according to the present invention.

Referring to FIG. 1, a functional block diagram of a defect integrated processing apparatus 100 according to a preferred embodiment of the present invention is shown. The defect integrated processing apparatus 100 includes a line-sensor camera 1 for picking up an image of a web 2 as an object to be inspected having a substantially constant width and traveling in one direction, an illuminator 3 for illuminating a zone on the web over which the camera 1 picks up the web image, and an image processing device 4A by which the image data picked up by the camera 1 are processed to perform an integrated processing of defects (if any) on the web.

The line-sensor camera 1 includes, for example, 1024 photoreceptors (e.g., a charge-coupled device (CCD)) arranged in an array along a line and disposed above a central portion in a width direction or a direction across the width of the web 2 and in a parallel relation to the width direction. The illuminator 3 is placed below (e.g., beneath) the web 2 so as to illuminate or light up a web zone R to be picked up by the camera 1 from a back side of the web 2.

As shown in FIG. 1, the image processing device 4A includes an image input portion 5 coupled to an output of the camera 1, a light-and-shade defect detecting portion 6, a minute defect detecting portion 7, and a low contrast light-and-shade defect detecting portion 8 which are coupled respectively to the image input portion 5, and a defect integrated processing portion 9 to which portions 6, 7, 8 are coupled in parallel and for providing outputs to portion 9.

As shown in FIG. 1, the image input portion 5 includes an analog-to-digital (A/D) converter 5a for performing an A/D conversion of an image signal outputted from the camera 1, and a memory 5b for storing, as image data, image signals produced by digitizing image analog signals obtained through a plurality of scans of the camera 1. As a result, the image signals picked up by the camera 1 are captured (e.g., provided to and stored) in the image processing device 4.

Figure 2:
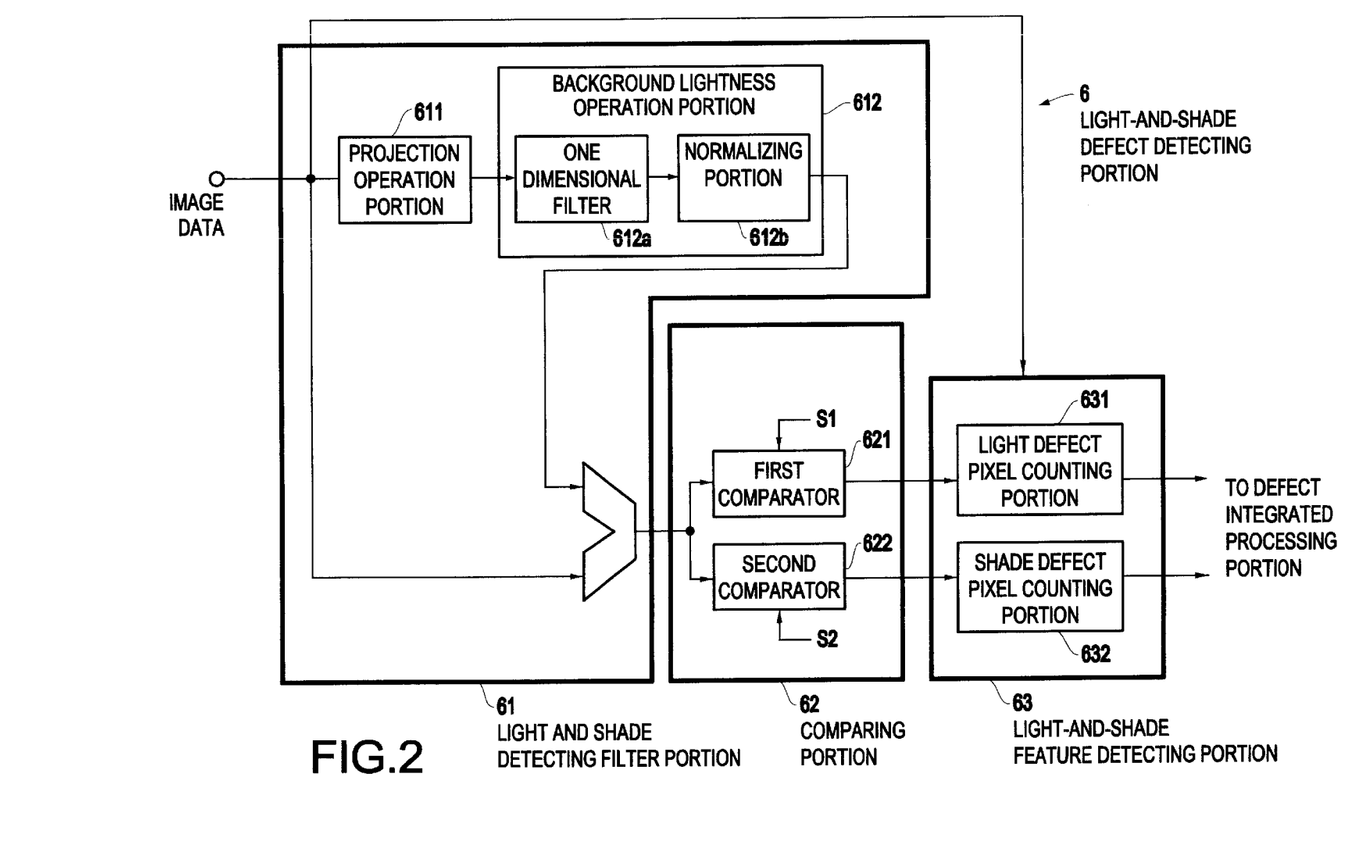
FIG. 2 is a functional block diagram showing a light-and-shade defect detecting portion 6 of the apparatus 100 of FIG. 1.

As shown in FIG. 2, the light-and-shade defect detecting portion 6 includes a light-and-shade detecting filter portion 61 coupled to an output of the image input portion 5, a comparing portion 62 coupled to an output of the light and shade detecting filter portion 61, and a light-and-shade feature detecting portion 63 coupled to an output of the comparing portion 62.

The light-and-shade detecting filter portion 61 includes a projection operation processing portion 611 coupled to the output of the image input portion 5, a background lightness processing portion 612, and a subtracter 613. The background lightness processing portion 612 includes a one-dimensional filter 612a coupled to an output of the projection processing portion 611 and a normalizing portion 612b coupled to an output of the one-dimensional filter 612a. The subtracter 613 has inputs coupled to outputs of the normalization portion 612b and the image input portion 5.

The comparing portion 62 is coupled to an output of the subtracter 613 and includes a first comparator 621 for comparing the output of the subtracter 613 with a first threshold value S1 and a second comparator 622 for comparing the output of the subtracter 613 with a second threshold value S2.

The light-and-shade feature detecting portion 63 includes a light defect pixel counting portion 631 coupled to an output of the first comparator 621, and a shade defect pixel counting portion 632 coupled to an output of the second comparator 622.

Figure 3:
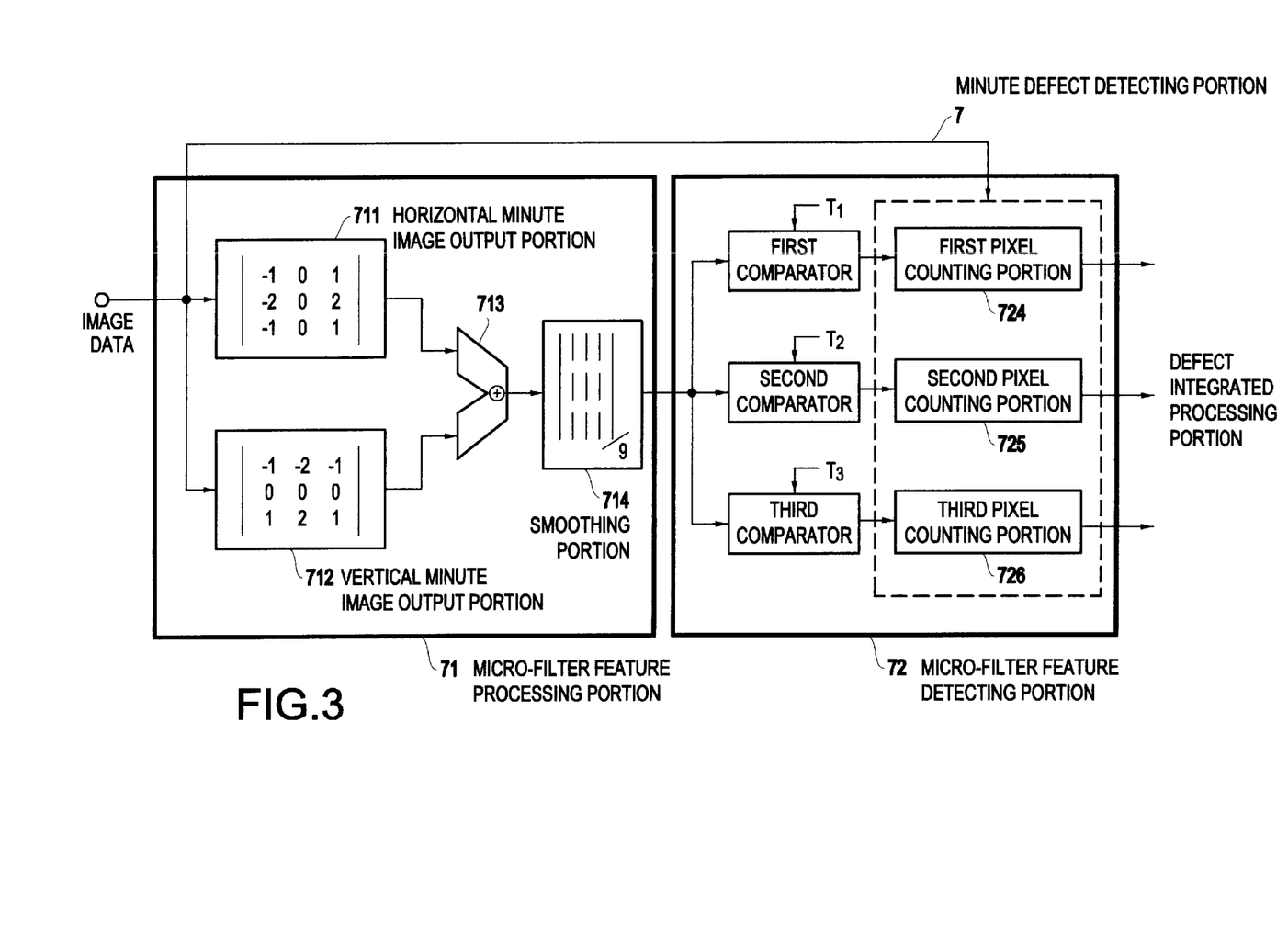
FIG. 3 is a functional block diagram showing a minute defect detecting portion 7 of the apparatus of 100 FIG. 1.

As shown in FIG. 3, the minute defect detecting portion 7 includes a micro-filter processing portion 71 and a micro-filter feature detecting portion 72. The micro-filter processing portion 71 includes a horizontal differentiated image output portion 711 and a vertical differentiated image output portion 712 both coupled to the output of the image input portion 5, an adder 713 coupled to the horizontal and vertical differentiated image output portions 711, 712, and a smoothing portion 714 coupled to an output of the adder 713.

The micro-filter feature detecting portion 72 includes a plurality (e.g,. three) comparators coupled respectively to an output of the smoothing portion 714. Specifically, a first comparator 721 compares the output of the smoothing portion 714 with a first preset value T1, a second comparator 722 compares the output of the smoothing portion 714 with a second preset value T2 (T2>T1), and a third comparator 723 compares the output of the smoothing portion 714 with a third preset value T3 (T3>T2).

The micro-filter feature detecting portion 72 further includes a first pixel counting portion 724 coupled to an output of the first comparator 721, a second pixel counting portion 725 coupled to an output of the second comparator 722, and a third pixel counting portion 726 coupled to an output of the third comparator 723.

Figure 4:
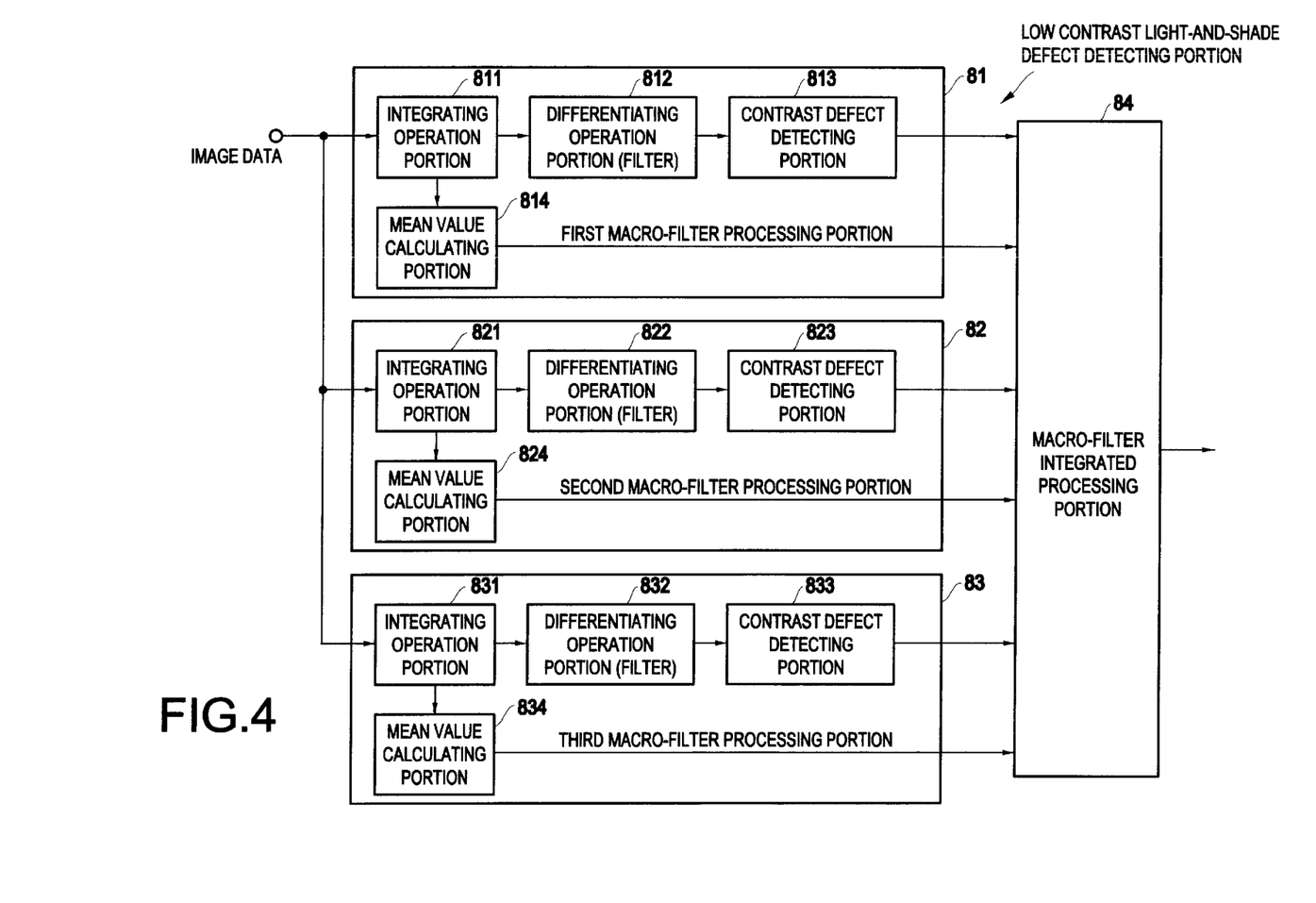
FIG. 4 is a functional block diagram showing a low contrast light-and-shade defect detecting portion 8 of the apparatus 100 of FIG. 1.

As shown in FIG. 4, the low contrast light-and-shade defect detecting portion 8 includes first, second and third macro-filter processing portions 81, 82, 83, respectively, and a macro-filter integrated processing portion 84 coupled to outputs of the three macro-filter processing portions 81, 82, 83.

Each of the macro-filter processing portions 81, 82, 83 respectively includes integrating an operation portion 811, 821, or 831, each having an integrating range (mesh) different from the other to produce an integrated image by performing addition within the integrating range, a differentiating operation portion 812, 822, or 832, each being coupled to an output of its corresponding integrating operation portion to produce a differentiated image by differentiating its corresponding integrated image, a contrast defect detecting portion 813, 823, or 833, each being coupled to an output of its corresponding differentiating operation; portion to detect low contrast defects based on its corresponding differentiated image by a threshold value different from the other, and an average value calculating portion 814, 824, or 834, each determining an average value of its corresponding integrated image.

Figure 5:
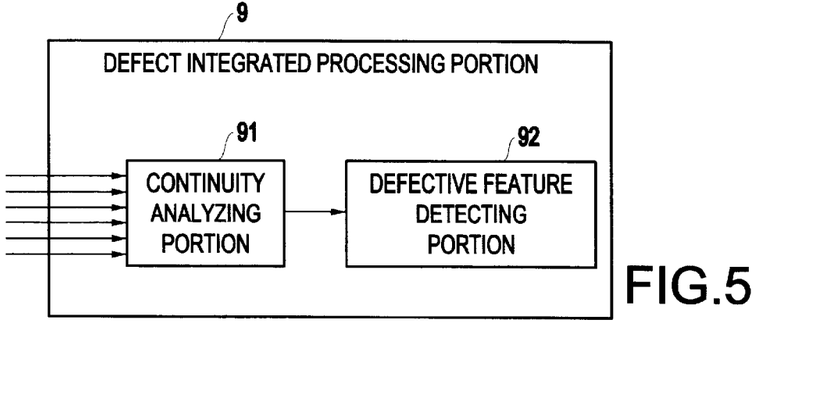
FIG. 5 is a functional block diagram showing a defect integrated processing portion 9 of the apparatus 100 of FIG. 1.

As shown in FIG. 5, the defect integrated processing portion 9 includes a connectivity analyzing portion 91 (e.g., coupled to outputs of the light defect pixel counting portion 631, shade defect pixel counting portion 632, first, second and third pixel counting portions 724–726, and macro-filter integrated processing portion 84), and a defective feature detecting portion 92 coupled to an output of the connectivity analyzing portion 91.

Hereinafter, the operation of the first preferred embodiment will be described.

Figure 6:
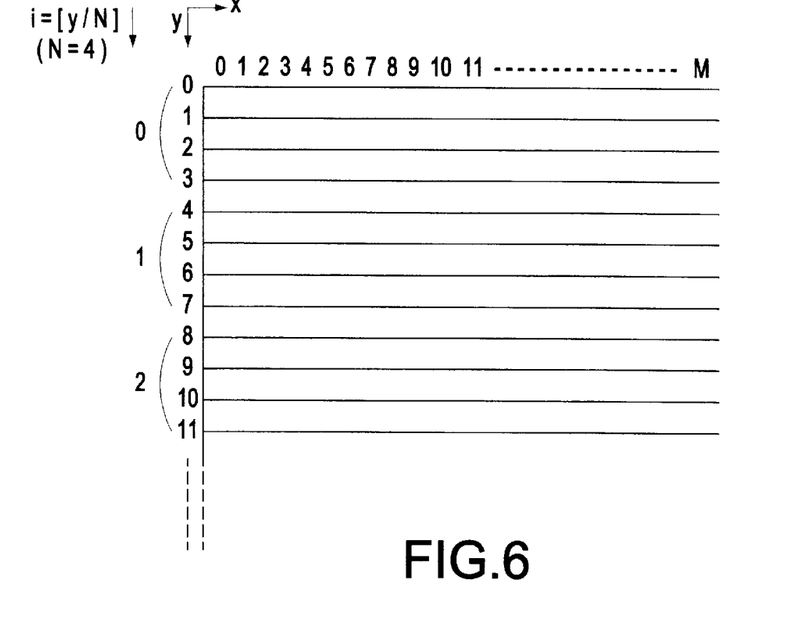
FIG. 6 is a schemnatic diagram showing an image data.

FIG. 6 is an image data structure captured into the memory 5b. In FIG. 6, a horizontal axis (X-axis) illustrates a region of data positions which is scanned through one scan of the line-sensor camera 1 and an X-coordinate indicates positions of the respective line-sensors which corresponds to positional coordinates on the web 2 in the width direction. In the example of FIG. 6, a positional coordinate of x=0 corresponds to an end or its neighboring portion of the web, whereas a positional coordinate of x=M corresponds to the other end or its neighboring portion of the web. In this embodiment, it is assumed that 1024 photoreceptors are used to pick up an image across the web's width with the position M=1024.

In FIG. 6, a vertical axis (Y-axis) indicates the number of scans of the camera 1 and has reference numerals 0 through 11 as the scan number affixed thereon For example, the scan number 0 indicates a first scan of the camera 1. In FIG. 6, i numbers are labeled, each being organized every N scans sequentially. The i number can be expressed by i=[y/N] with the Gaussian notation "[ ]".

Next, the light-and-shade defect detecting portion 6 will be described in connection with its operation.

The projection operation portion 611 in the light-and-shade detecting filter portion 61, as shown in FIG. 2, will obtain a projection by using scan data of N lines (N×M) at a time from the memory, as being representative of its operation in FIG. 6.

Figure 7:
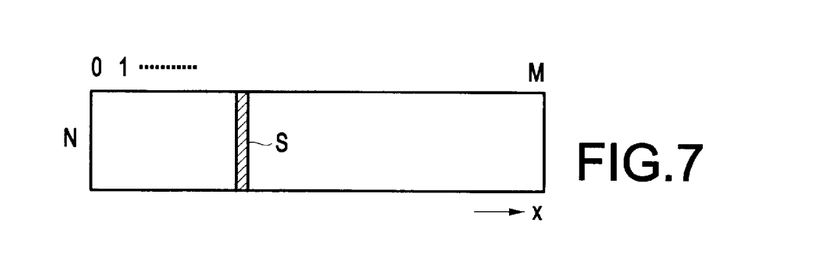
FIG. 7 is a schematic diagram showing a data structure obtained through a number
Figure 8:
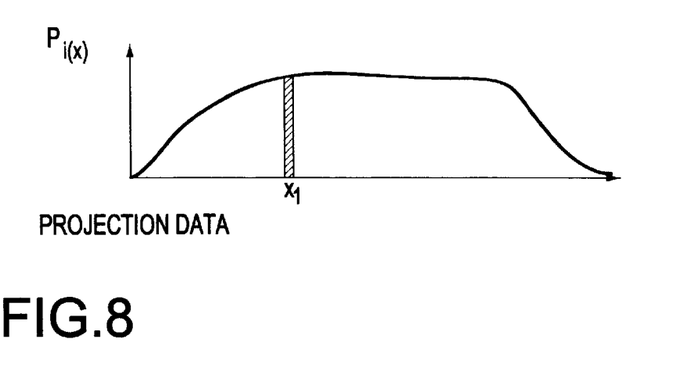
FIG. 8 is a schematic diagram showing a projection data.
Figure 9:
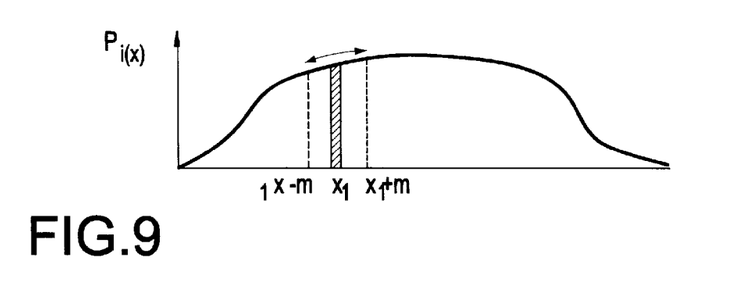
FIG. 9 is a schematic diagram showing a smoothing processing of the projection data.

As shown in FIG. 7, N image data at each x-coordinate are added together to create a hatching portion S (i.e., image data at a predetermined position in the transverse direction of the object to be inspected are added together until the number of its image data reaches a predetermined number), thereby providing a projection data as shown in FIG. 8.

Figure 10:
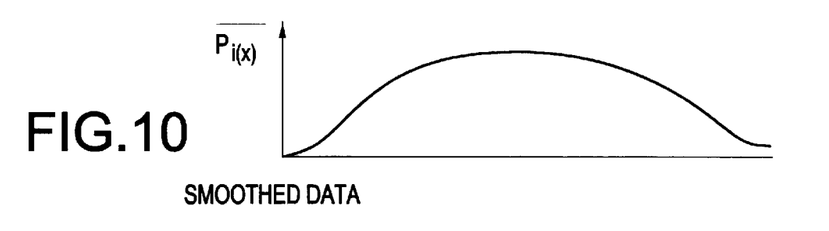
FIG. 10 is a schematic diagram showing a smoothed data.
Figure 14:
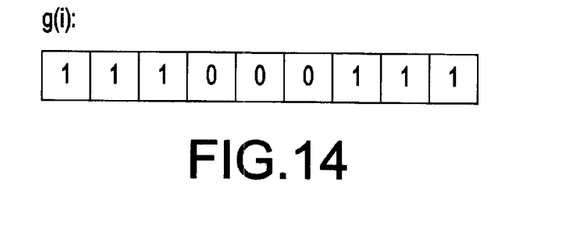
FIG. 14 is a schematic diagram showing an exemplary one-dimensional filter.

This operation or calculation is expressed by the following equation (1):

$$Pi = \Sigma f(x, y) \tag{1}$$

wherein i=[y/N], N defines a number of lines to be added together, with this addition being performed up to the N line numbers counting from y=N·i (i.e., up to N·i+N−1). Next, the one-dimensional filter 612a smooths the projection data, produced from the projection operation portion 611, in a range between +m and −m from its x-coordinate ($x_1$) in the x-axis direction, thereby producing a smoothed data as shown in FIG. 10. This operation or calculation is provided by the following equation (2):

$$\overline{Pi}(x) = (\Sigma Pi(x-m+j) \cdot g(j) / (\Sigma g(j))) \tag{2}$$

wherein the addition is performed with j=0~2 m, and g is representative of, for example, a filter function, as shown in FIG. 14, but it may be replaced by a constant.

Figure 11:
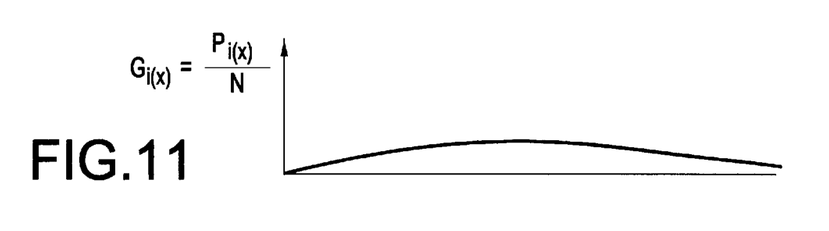
FIG. 11 is a schematic diagram showing a normalized data.

The normalizing portion 612a divides the smoothed data by the number N of lines added together as above, thereby obtaining a background lightness Gi(x), as shown in FIG. 11. This operation is given by the following equation (3):

$$Gi=Pi(x)/N \qquad (3)$$

The subtracter 613 subtracts the obtained background lightness Gi(x) from image data f(x,y) newly inputted from the camera 1 to the image input portion 5. This operation or calculation is provided by the following equation (4):

$$F(x,y)=f(x,y)-Gi(x), \; i=[y/N] \qquad (4)$$

Figure 12:
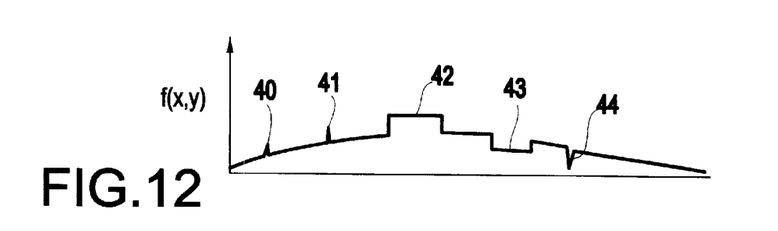
FIG. 12 is a schematic diagram showing an image data inputted from an image input portion.
Figure 13:
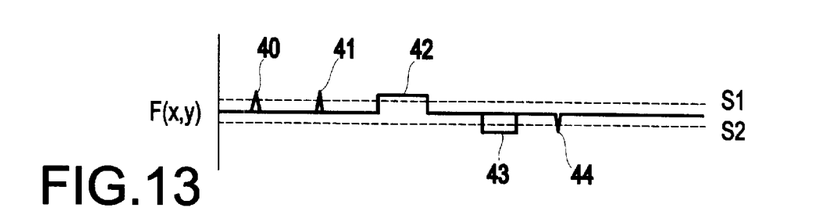
FIG. 13 is a schematic diagram showing an image data after removal of a background lightness.

With this operation, the inputted image data f(x,y), as shown in FIG. 12, is changed into or expressed by a function F(x,y) from which variations of the background lightness are eliminated; as shown in FIG. 13. In this case, depending on the number of scans of the line-sensor camera 1, the number of data to be subjected to the filter processing may be increased. As a result, the length of the smoothed data obtained by the filter can be set larger than the size of the defects. Therefore, adverse affects of the defects' sizes, caused by eliminating the background variations, can be reduced.

The first comparator 621 compares this function F(x,y) with the first threshold value S1 and then it is judged to be a light defect if the function F(x,y) is larger than the first threshold value S1 . Also, the second comparator 622 compares the function F(x,y) with the second threshold value S2 and then it is judged to be a shade defect if the function F(x,y) is lower (e.g., larger in its absolute value) than the second threshold value S2.

In the light-and-shade feature detecting portion 63, a lattice mesh pattern of meshes on an image is established, each mesh being a predetermined size (16×16 pixels) set in the image. The light defective pixel counting portion 631 counts pixels $S_H(i,j)$ which are judged to be light defects within their corresponding meshes, and then outputs the resultant count to the defect integrated processing portion 9. Similarly, the shade defective pixel counting portion 632 counts pixels $S_L(i,j)$ which are decided to be shade defects within their corresponding meshes, and then outputs the resultant count to the defect integrated processing portion 9.

Next, the minute defect detecting portion 7 will be described in connection with its operation.

The micro-filter processing portion 71 calculates a horizontal differentiated image and a vertical differentiated image in connection with an objective image to be processed and includes the image date f(x,y). The horizontal differentiated image output portion 711 performs the calculation in connection with the objective image f(x,y) to be processed as follows:

HORIZONTAL DIFFERENTIATED IMAGE:

$$F_H(x, y) = /(f(x+1, y-1) - f(x-1, y-1)) + \qquad (5)$$
$$2x(f(x+1, y) - f(x-1, y)) + (f(x+1, y+1) - f(x-1, y+1))/$$

Also, the vertical differentiated image output portion 712 performs the calculation in connection with the objective image to be processed f(x,y) as follows:

VERTICAL DIFFERENTIATED IMAGE:

$$F_V(x, y) = /(f(x-1, y+1) - f(x-1, y-1)) + \qquad (6)$$
$$2x(f(x, y+1) - f(x, y-1)) + (f(x+1, y+1) - f(x+1, y-1))/$$

The adder 713 calculates an added image $F_A(x,y)$, as follows, which is an average of sum of the vertical differentiated image $F_V(x,y)$ and horizontal differentiated image $F_H(x,y)$ respectively obtained as above.

$$F_A(x,y)=(F_v(x,y)+F_H(x,y))/2 \qquad (7)$$

The smoothing portion 714 obtains a micro-filtered image $F_M(x,y)$ through a smoothing filter processing of the added image $F_A(x,y)$ as follows:

MICRO-FILTERED IMAGE:

$$F_M(x, y) = (F_A(x-1, y-1) + \qquad (8)$$
$$F_A(x, y-1) + F_A(x+1, y-1) + F_A(x-1, y)$$
$$F_A(x, y) + F_A(x-1, y)$$
$$F_A(x-1, y+1) + F_A(x, y+1)$$
$$F_A(x=1, y+1))/9$$

The micro-filter feature detecting portion 72 performs the defect detection by digitizing into binary values (or binary-digitizing) outputs of the smoothing portion 714 using the first, second and third comparators 721, 722, 723, each having a threshold value or preset value (T1, T2, T3 with a relationship of T1<T2<T3). Subsequently, the first, second and third pixel counting portions 724, 725, 726 obtain, respectively, the numbers $S_M^{(1)}(i,j)$, $S_M^{(2)}(i,j)$, $S_M^{(3)}(i,j)$ of pixels present within each lattice mesh of the predetermined size (16×16 pixels) established on the image, and then output them to the defect integrated processing portion 9.

Next, the low contrast light-and-shade defect detecting portion 8 will be described in connection with its operation.

In the first macro-filter processing portion 81, the integrating operation portion 811 establishes a mesh pattern of meshes, each mesh being m×× n pixels, on an inputted image, and then adds together the image data within each mesh to obtain an integrated image F(x,y).

This integrated image F(x,y) can be expressed by the following equation (9):

$$F(x,y)=\Sigma\Sigma f(mx+x', \; ny+y') \qquad (9)$$

wherein a first Σ of the right side of the above equation (9) performs an addition of x'(the number of m) from 0 to m−1, and a second Σ of the right side of the above equation (9)) performs an addition of y'(e.g., the number of m) from 0 to m−1.

The differentiating operation portion 812 produces a differentiated image D(x,y) by obtaining a difference of values between two integrated images F(x,y) in two meshes which are spaced from each other by a predetermined interval, as follows:

$$D(x,y)=/F(x+\Delta x,y+\Delta y)-F(x-\Delta x,y-\Delta y)/ \qquad (10)$$

wherein Δx and Δy respectively represent a distance between the meshes, each being an appropriate positive integer.

The contrast defect detecting portion 813 determines the existence of a defect when the value of D(x,y) produced from the equation (10) becomes larger than a predetermined threshold value T, as expressed by the following equation (11):

$$D(x,y) > T(=t_{s1}) \quad (11)$$

On the other hand, the mean (or average) value calculating portion 814 calculates an average A(x) of the integrated images F(x,y) by the following equation (12):

$$A(x) = (\Sigma F(x,y'))/N \quad (12)$$

wherein the addition is performed from y'=N·i to N·i+N−1, the i is expressed by i=[y/N] with the Gaussian notation [ ], and N is any average length.

Each of the second and third macro-filter processing portions 82 and 83 also performs a similar processing to that performed by the first macro-filter processing portion 81. However, the meshes (integrating ranges) employed in the respective integrating operations 821, 831 and the threshold values T employed in the respective defect detecting portion 823, 833 are different from those employed in the first macro-filter processing portion 81.

In this embodiment, the mesh (e.g., the integrating range) employed in the first macro-filter processing portion 81 uses any one of, for example, 8×8, 8×16, 16×8, or 16×16 matrix of pixels. Further, the integrating range of the second macro-filter processing portion is larger than that of the first macro-filter processing portion, and the integrating range of the third macro-filter processing portion is larger than that of the second filter processing portion.

Next, the macro-filter integrated processing portion 84 will be described in connection with its operation.

The macro-filter integrated processing portion 84 performs the following processing to the respective defect positions detected in the first, second and third macro-filter processing portions 81, 82, 83.

Here, it is assumed that, correspondingly to the integrated image produced in the first, second and third macro-filter processing portions 81, 82, 83, the macro-filter integrated processing portion 84 employs $S^{(1)}(x,y)$, $S^{(2)}(x,y)$, and $S^{(3)}(x,y)$ as integrated images and $t_{s1}$, $t_{s2}$, $t_{s3}$ as defect detection threshold values. Further, defect matrixes, each of which defines the presence and the absence of defects on the image f(x,y), are expressed by: $D^{(1)}(x,Y)$, $D^{(2)}(x,y)$, and $D^{(3)}(x,y)$. Also, defective feature matrixes, each of which defines a defective feature, are expressed by: $V^{(1)}(x,y)$, $V^{(2)}(x,y)$, and $V^{(3)}(x,y)$. Further, an average of each column on each integrated image is respectively expressed by: $A^{(1)}(x)$, $A^{(2)}(x)$, and $A^{(3)}(x)$.

In consideration of the above, the macro-filter integrated processing portion 84 performs the following operation to eliminate an affect of defects obtained in the first macro-filter processing portion on the second and third macro-filter processing portions. In the following equation (13), it is assumed that m=1, 2, 3 and the operation procedure is performed in a sequence beginning from a smaller value of m to a larger value thereof.

$$S^{(m)}(x,y) = S^{(m)}(x,y) - \Sigma V(k,1)^{(1)} \quad (13)$$

wherein, the addition of the second term on the right side performs in connection with each value (k, 1) in the mesh used for the calculation of the first macro-filter processing portion included in $S^{(m)}(x,y)$.

In a preparatory stage as mentioned above, the defect detection processing is performed as follows:

$$\Delta S^{(m)}(x,y) = S^{(m)}(x+\Delta x, y+\Delta y) - S^{(m)}(x-\Delta x, y-\Delta y) \quad (14)$$

wherein, if it is found to be $/\Delta S^{(m)}(x,y)/ > t_x^{(m)}$, the following processing will be performed.

$$S_+ = S^{(m)}(x+\Delta x, y+\Delta y) - A^{(m)}(x+\Delta x, y+\Delta y)$$

$$S_- = S^{(m)}(x-\Delta x, y-\Delta y) - A^{(m)}(x-\Delta x, y-\Delta y) \quad (15)$$

Also, if it is found to be $/S_-/ > /S_+/$, then the defect matrix will be $D^{(m)}(x-\Delta x, y-\Delta y)=1$, $V^{(m)}(x,y)=S_-$ with $S^{(m)}(x-\Delta x, y-\Delta y)$ being defects.

On the other hand, if it is found to be $/S_-/ \leq /S_+/$, then the defect matrix will be $D^{(m)}(x+\Delta x, y+\Delta y)=1$, $V^{(m)}(x,y)=S_+$ with $S^{(m)}(x+\Delta x, y+\Delta y)$ being defects.

Next, the defect integrated processing portion 9 will be described in connection with the operation of connectivity analyzing portion 91.

The connectivity analyzing portion 91 synthesizes, every size of predetermined meshes (16×16 lattice pattern of pixels), a plurality of defects of: the respective light and shade defective pixels $S_H(i,j)$ and $S_L(i,j)$ produced from the light and shade defect pixel counting portions 631, 632 of the light-and-shade feature detecting portion 6; the respective pixels $S_M^{(1)}(i,j)$, $S_M^{(2)}(i,j)$, $S_M^{(3)}(i,j)$ produced from the first, second and third pixel counting portions of the micro-filter feature detecting portion 72; and the defect matrix $D^{(m)}(x+\Delta x, y+\Delta y)$ produced from the macro-filter integrated processing portion, so as to conduct the connectivity analysis of the defects.

Figure 15:
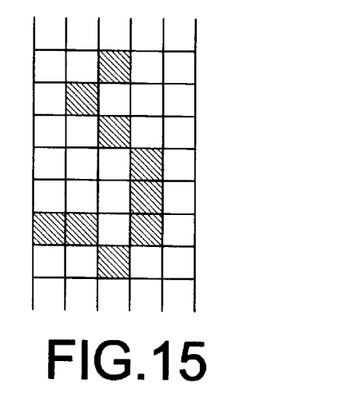
FIG. 15 is a schemnatic diagram showing an exemplary connectivity of a defect obtained by a connectivity analysis.

An example of this continuous defect is shown in FIG. 15. This connectivity analysis is performed by deciding (e.g., judging) whether or not a connectivity is present between any one of mesh as a central one and eight (8) meshes surrounding the central mesh (e.g., an 8-linkage rule).

The defective feature detecting portion 92 calculates a sum of various features representative of: the number of light defective pixels $S_H(i,j)$, the number of shade defective pixels $S_L(i,j)$, the numbers of the respective pixels $S_M^{(1)}(i,j)$, $S_M^{(2)}(i,j)$, $S_M^{(3)}(i,j)$ as being the macro-filter features, the macro-filter features $V^{(1)}(i,j)$, $V^{(2)}(i,j)$, $V^{(3)}(i,j)$ [corresponding to $V^{(m)}(x,y)$].

These features include, for example, an area, a height and a width of a Bounding Box (e.g., rectangle), an aspect ratio, a compactness, a structure parameter, an edge strength, and an average density which correspond to the numbers of various defective pixels constituting one defect.

Here, the compactness C is obtained as follows:

$$C = 4\sqrt{(SB/SM^2)} \quad (16)$$

wherein, SB is the total number of $S_H(i,j)$ or $S_L(i,j)$ and SM is the total number $S_M^{(1)}(i,j)$.

Also, the structure parameter O is obtained as follows:

$$O = \sqrt{((Wx \cdot (Wy)/S)} \quad (17)$$

wherein Wx is a height of the defect, Wy is a width of the defect, and S is the number of meshes included in the defect.

Further, the edge strength $T^\alpha$ is obtained as follows:

$$T^\alpha = \frac{S_1 \cdot T_1^{\alpha-1}}{S_1 \cdot T_1^{\alpha-1} + S_2 \cdot T_2^{\alpha-1} + S_3 \cdot T_3^{\alpha-1}} T_1^\alpha + \frac{S_2 \cdot T_2^{\alpha-1}}{S_1 \cdot T_1^{\alpha-1} + S_2 \cdot T_2^{\alpha-1} + S_3 \cdot T_3^{\alpha-1}} T_2^\alpha + \frac{S_3 \cdot T_3^{\alpha-1}}{S_1 \cdot T_1^{\alpha-1} + S_2 \cdot T_2^{\alpha-1} + S_3 \cdot T_3^{\alpha-1}} T_3^\alpha \quad (18)$$

wherein, $S_1$, $S_2$, $S_3$ are respectively the total numbers of pixels $S^{(1)}(i,j)$, $S^{(2)}(i,j)$, $S^{(3)}(i,j)$ as the micro-filtered features, $T_1, T_2, T_3$ correspond respectively to the threshold values T1, T2, T3, and $\alpha$ is a constant.

As described above, the defect integrated processing apparatus according to the present invention includes an image pick-up device for picking up an image of an object to be inspected to output an image data; a light-and-shade defect detecting portion for detecting light-and-shade defects on the object based on the light-and-shade information of the image data obtained through the image pick-up device; a minute defect detecting portion for detecting edges and minute defects on the object by performing a differential processing of the image data obtained through the image pick-up device; a low contrast light-and-shade defect detecting portion for detecting low contrast light-and-shade defects on the object by performing a differential processing of an integrated image obtained through an integral processing of the image data obtained through the image pick-up device; and a defect integrated processing portion for obtaining an integrated information involving defects by performing a processing, in an integrated fashion, of the respective defects of the light-and-shade defects obtained through the light-and-shade defect detecting portion, the minute defects obtained through the minute defect detecting portion, and the low contrast light-and-shade defects obtained through the low contrast light-and-shade defect detecting portion.

As a result, various defects will be processed in an integrated fashion to allow a detailed detection to obtain an accurate defect information about numbers, positions, and sizes thereof.

While the invention has been described in terms of a single preferred embodiment, those skilled in the art will recognize that the invention can be practiced with modification within the spirit and scope of the appended claims.

What is claimed is:

1. A defect integrated processing apparatus for use in picking up an image of an object to be inspected to obtain an image data and then, based on the image data, inspecting defects of the object in an integrated fashion, comprising:

an image pick-up device for picking up an image of an object to output an image data;

a light-and-shade defect detecting portion for detecting light-and-shade defects on the object based on the image data obtained by said image pick-up device;

a minute defect detecting portion for detecting edges and minute defects on the object by performing a differential processing of the image data obtained by said image pick-up device;

a low contrast light-and-shade defect detecting portion for performing a differential processing of an integrated image obtained by an integral processing of the image data obtained by said image pick-up device;

a defect integrated processing portion for obtaining an integrated information involving defects by performing a process, in an integrated fashion, of the respective defects of the light-and-shade defects obtained by said light-and-shade defect detecting portion, the minute defects obtained from said minute defect detecting portion, and the low contrast light-and-shade defects obtained by said low contrast light-and-shade defect detecting portion; and a connectivity analyzing portion for analyzing a connectivity among the light-and-shade defects obtained by said light-and-shade defect detecting portion, the minute defects obtained by said minute defect detecting portion, and the low contrast light-and-shade defects obtained by said low contrast light-and-shade defect detecting portion, wherein said defect integrated processing portion counts a detected defect no more than one time.

2. The defect integrated processing apparatus as claimed in claim 1, wherein said light-and-defect detecting portion includes:

a projection operation portion for calculating a projection data by adding together a predetermined number of image data at a given position along a certain direction of the object, said image data being obtained by said image pick-up device; and a background operation portion for calculating a background lightness across a width direction of the object, based on the projection data obtained by said projection operation portion;

a difference operation portion for removing variations of the background lightness across the width direction obtained by said background lightness operation portion from the image data obtained through said image pick-up device by subtracting a former background lightness from a latter image data.

3. The defect integrated processing apparatus as claimed in claim 2, wherein said background lightness operation portion includes:

a filter for performing a smoothing processing of the projection data across the width direction of the object obtained by said projection operation portion; and a normalizing portion for calculating the background lightness by dividing the smoothed data through said filter by the predetermined number used for adding together the image data at a given position.

4. The defect integrated processing apparatus as claimed in claim 2, further comprising a comparing portion for comparing the output of said difference operation portion with a predetermined value.

5. The defect integrated processing apparatus as claimed in claim 3, further comprising a comparing portion for comparing the output of said difference operation portion with a predetermined value.

6. The defect integrated processing apparatus as claimed in claim 1, wherein said light-and-shade defect detecting portion includes a light-and-shade feature detecting portion for detecting light-and-shade features by establishing on an image based on the image data a mesh pattern of meshes, each mesh being a predetermined size, and then counting the number of pixels, each pixel being present within each mesh and larger than a light defect threshold value and similarly counting the number of pixels, each pixel being present within each mesh and smaller than a shade defect threshold value.

7. The defect integrated processing apparatus as claimed in claim 1, wherein said low contrast light-and-shade defect detecting portion comprises a macro-filter processing portion, said macro-filter processing portion including:

an integrating operation portion for obtaining an integrated image by dividing an image formed of image data outputted from said image pick-up device into a plurality of meshes which have equivalent areas to each other and then adding together the image data present within each divided mesh;

a differentiating operation portion for obtaining a differentiated image by performing a difference operation at a predetermined interval between meshes in connection with the integrated image obtained by said integrating operation portion; and a contrast defect detecting portion for detecting low contrast defects based on the differentiated image obtained by said differentiating operation portion.

8. The defect integrated processing apparatus as claimed in claim 7, wherein said low contrast light-and-shade defect detecting portion includes a plurality of macro-filter processing portions, said macro-filter processing portions being different from each other in mesh size in a range of which the addition of the image data is performed by said integrating operation portion and different from each other in a threshold value which is varied depending on said mesh size and based on which defects are detected by said contrast defect detecting portion.

9. The defect integrated processing apparatus as claimed in claim 8, wherein said low contrast defect detecting portion further includes a macro-filter integrated processing portion, said macro-filter integrated processing portion being adapted for, among meshes of different sizes in each range of which the addition of the image data is performed by said integrating operation portion, subtracting, from a value of the integrated image having defects and obtained through a smaller mesh size, its average value so as to obtain its subtracted value, subtracting the subtracted value from a value of the integrated image obtained through a larger mesh size so as to obtain a differentiated image in the larger mesh size, and, based on the differentiated image, judging and detecting low contrast defects in the larger mesh size.

10. The defect integrated processing apparatus as claimed in claim 9, wherein said macro-filter integrated processing portion is adapted for outputting to said defect integrated processing portion the respective values, as macro-defect features, based on the integrated images involving defects obtained by said macro-filter integrated processing portion as well as information of mesh positions.

11. The defect integrated processing apparatus as claimed in claim 1, wherein said minute defect detecting portion includes:

a minute defect detecting spatial filter processing portion for obtaining vertical and horizontal differentiated images of an image based on the image data, calculating an added image which is an average of a sum of the vertical and horizontal differentiated images, and highlighting a minute defect by smoothing the added image; and a micro-filter feature detecting portion for digitizing into binary values the output value from said minute defect detecting spatial filter processing portion, establishing a mesh pattern of meshes each having a predetermined size on the image based on the image data, and counting the number of pixels, each pixel having said output value which is larger than the threshold value at each mesh.

12. The defect integrated processing apparatus as claimed in claim 11, wherein the threshold value includes a plurality of kinds of values, at each of which the number of pixels is counted.

13. The defect integrated processing apparatus as claimed in claim 1, wherein said object to be inspected includes a web having a substantially constant width and traveling in a constant direction, and wherein said image pick-up device includes a line-sensor camera which is opposed to said object and disposed across the width direction thereof.

14. The defect integrated processing apparatus as claimed in claim 1, wherein said defect integrated processing portion includes:

a defect feature calculating portion for calculating a predetermined feature based on a defect obtained by said connectivity analyzine portion.

15. A defect integrated processing apparatus, comprising:

a first-type defect detecting portion for detecting first-type defects on an object based on image data related to said object and inputted to said first-type defect detecting portion;

a second-type defect detecting portion for detecting edges and second-type defects on the object by performing a differential processing of the image data;

a third-type defect detecting portion for performing a differential processing of an integrated image obtained by an integral processing of the image data;

a defect integrated processing portion for obtaining an integrated information involving defects by performing a processing, in an integrated fashion, of the respective defects of the first-type defects obtained by said first-type defect detecting portion, the second-type defects obtained from said second-type defect detecting portion, and the third-type defects obtained by said third-type defect detecting portion; and a connectivity analyzing portion for analyzing a connectivity among the first-type defects obtained by said first-type defect detecting portion, the second-type defects obtained by said second-type defect detecting portion, and the third-type defects obtained by said third- type defect detecting portion, wherein said defect integrated processing portion counts a detected defect no more than one time.

16. The defect integrated processing apparatus as claimed in claim 15, further comprising:

an image pick-up device for picking up an image of the object to output the image data to said first-type defect detecting portion.

17. The defect integrated processing apparatus as claimed in claim 15, wherein said first-type defect detecting portion comprises a light-and-shade defect detecting portion, said second-type defect detecting portion comprises a minute defect detecting portion, and said third-type defect detecting portion comprises a low contrast light-and-shade defect detecting portion.

18. An image processing apparatus for a defect integrated processing system, comprising:

a first-type defect detecting portion for detecting first-type defects on an object based on image data related to said object and inputted to said first-type defect detecting portion;

a second-type defect detecting portion for detecting edges and second-type defects on the object by performing a differential processing of the image data;

a third-type defect detecting portion for performing a differential processing of an integrated image obtained by an integral processing of the image data;

a defect integrated processing portion for obtaining an integrated information involving defects by performing a processing, in an integrated fashion, of the respective defects of the first-type defects obtained by said first-type defect detecting portion, the second-type defects obtained from said second-type defect detecting portion, and the third-type defects obtained by said third-type defect detecting portion; and a connectivity analyzing portion for analyzing a connectivity among the first-type defects obtained by said first-type defect detecting portion, the second-type defects obtained by said second-type defect detecting portion, and the third-type defects obtained by said third-type defect detecting portion, wherein said defect integrated processing portion counts a detected defect no more than one time.

19. A defect integrated processing method, comprising:

based on light-and-shade information of an image data of an object detecting light-and-shade defects of the object;

performing a differential processing of the image data to detect edges and minute defects on the object;

performing an integral processing of the image data to obtain an integrated image and then performing a differential processing of the obtained integrated image to detect low contrast light-and-shade defects;

performing a processing in an integrated fashion of the light-and-shade defects, the minute defects, and the low contrast light-and-shade defects to obtain an integrated information of defects detected; and analyzing a connectivity among the light-and-shade defects obtained by said light-and-shade defect detecting portion, the minute defects obtained by said minute defect detecting portion, and the low contrast light-and-shade defects obtained by said third-type defect detecting portion, wherein said defect integrated processing counts a detected defect no more than one time.

20. The method according to claim 19, further comprising:

picking up an image of the object to be inspected to obtain the image data.

21. A defect integrated processing apparatus for use in picking up an image of an object to be inspected to obtain an image data and then, based on the image data, inspecting defects of the object in an integrated fashion, comprising:

an image pick-up device for picking up an image of an object to output an image data;

a light-and-shade defect detecting portion for detecting light-and-shade defects on the object based on the image data obtained by said image pick-up device;

a minute defect detecting portion for detecting edges and minute defects on the object by performing a differential processing of the image data obtained by said image pick-up device;

a low contrast light-and-shade defect detecting portion for performing a differential processing of an integrated image obtained by an integral processing of the image data obtained by said image pick-up device;

a defect integrated processing portion for obtaining an integrated information involving defects by performing a process, in an integrated fashion, of the respective defects of the light-and-shade defects obtained by said light-and-shade defect detecting portion, the minute defects obtained from said minute defect detecting portion, and the low contrast light-and-shade defects obtained by said low contrast light-and-shade defect detecting portion; and a connectivity analyzing portion for analyzing a connectivity among at least two defects selected from the light-and-shade defects obtained by said light-and-shade defect detecting portion, the minute defects obtained by said minute defect detecting portion, and the low contrast light-and-shade defects obtained by said low contrast light-and-shade defect detecting portion, wherein said defect integrated processing portion counts a detected defect no more than one time.

* * * * *